US008420548B2

(12) United States Patent
Abbadie

(10) Patent No.: US 8,420,548 B2
(45) Date of Patent: Apr. 16, 2013

(54) METHOD FOR TREATING GERMANIUM SURFACES AND SOLUTIONS TO BE EMPLOYED THEREIN

(75) Inventor: Alexandra Abbadie, Le Versoud (FR)

(73) Assignee: Soitec, Bernin (FR)

( * ) Notice: Subject to any disclaimer, the term of this patent is extended or adjusted under 35 U.S.C. 154(b) by 241 days.

(21) Appl. No.: 12/808,353

(22) PCT Filed: Nov. 5, 2008

(86) PCT No.: PCT/IB2008/003039
§ 371 (c)(1),
(2), (4) Date: Jun. 15, 2010

(87) PCT Pub. No.: WO2009/090454
PCT Pub. Date: Jul. 23, 2009

(65) Prior Publication Data
US 2010/0267244 A1    Oct. 21, 2010

(30) Foreign Application Priority Data

Dec. 21, 2007 (EP) .................................... 07291590

(51) Int. Cl.
*H01L 21/302* (2006.01)
*H01L 21/461* (2006.01)
(52) U.S. Cl.
USPC .......................................... 438/745; 438/752
(58) Field of Classification Search ........................ None
See application file for complete search history.

(56) References Cited

U.S. PATENT DOCUMENTS

| | | | | |
|---|---|---|---|---|
| 3,818,262 | A | * | 6/1974 | Forgue ............................ 315/11 |
| 3,869,313 | A | | 3/1975 | Jones et al. |
| 7,250,085 | B2 | * | 7/2007 | Abbadie et al. .................. 134/2 |
| 7,641,738 | B2 | * | 1/2010 | Abbadie et al. .................. 134/2 |

OTHER PUBLICATIONS

Abbadie, A., et al., "Evaluation of different etching techniques in order to reveal dislocations in thick Ge layers," ECS Transactions, vol. 6, No. 4, May 2007, pp. 263-269.
Abbadie, A., et al., "An efficient wet-cleaning of SiGe virtual substrates and of thick, pure Ge layers on Si(001) after a chemical mechanical planarization step," Microelectronic Eng'g., vol. 83, No. 10, Oct. 1, 2006, pp. 1986-1993.
Clawson A.R., "Guide to references on III-V semiconductor chemical etching," Materials Science and Eng'g, vol. 31, No. 1-6, Jan. 15, 2001, pp. 1-438.
Hsin-Chiao, Luan, et al., "High-quality Ge epilayers on Si with low threading-dislocation densities," Applied Physics Letters, vol. 75, No. 19, Nov. 8, 1999, pp. 2909-2911.
Li, Qiming, et al., "Heteroepitaxy of high-quality Ge on Si by nanoscale Ge seeds grown through a thin layer of SiO2," Applied Physics Letters, vol. 85, No. 11, Sep. 13, 2004, pp. 1928-1930.
Malta, D.P., et al., "Low-defect-density germanium on silicon obtained by a novel growth phenomenon," Applied Physics Letters, vol. 60, No. 7, Feb. 17, 1992, pp. 844-846.

(Continued)

*Primary Examiner* — Duy Deo
(74) *Attorney, Agent, or Firm* — TraskBritt

(57) ABSTRACT

The present invention concerns an improved method for treating germanium surfaces in order to reveal crystal defects.

9 Claims, 2 Drawing Sheets

OTHER PUBLICATIONS

Sun, Yun, et al., "Surface termination and roughness of Ge(100) cleaned by HF and HCl solutions," Applied Physics Letters 88, 021903 (2006), three (3) pages.

PCT International Search Report, International Application No. PCT/IB2008/003039, Jul. 21, 2009, five (5) pages.

Written Opinion of the International Searching Authority, International Application No. PCT/IB2008/003039, Jul. 21, 2009, five (5) pages.

SECCO, Dislocation Etch for (100) Planes in Silicon, Journal of the Electrochemical Society 119, No. 7, pp. 948-951 (1972).

* cited by examiner

METHOD FOR TREATING GERMANIUM SURFACES AND SOLUTIONS TO BE EMPLOYED THEREIN

CROSS-REFERENCE TO RELATED APPLICATIONS

This is a national phase entry under 35 U.S.C. §371 of International Patent Application PCT/IB2008/003039, filed Nov. 5, 2008, published in English as International Patent Publication WO 2009/090454 A2 on Jul. 23, 2009, which claims the benefit under Article 8 of the Patent Cooperation Treaty to European Patent Application Serial No. 07291590.3, filed Dec. 21, 2007, the entire disclosure of each of which is hereby incorporated herein by this reference.

TECHNICAL FIELD

The present invention relates to a method of treating germanium surfaces, such as surfaces of germanium wafers, including GeOI structures. In particular, the present invention relates to a method for characterizing and visualizing defects on such surfaces by carrying out a surface treatment using specific solutions in order to enable a highly satisfactory characterization of the substrate surface, in particular by enlarging the size of defects in order to make them visible and to allow their optical observation.

BACKGROUND

Generally, crystalline defects in substrates for microelectronic devices are highly undesirable because of their negative impact on functionality and reliability of integrated circuits formed on such substrates. For the delineation of crystalline defects and accordingly for the characterization of the quality of such substrates, structural etching solutions are widely employed. With respect to crystalline defects, the etch rate of structural etching solutions differ, leading to the production of hillocks or etch pits, which can then be visually observed.

Germanium (Ge) has increasingly been studied in relation to its use as substrate for microelectronic devices, due to the intrinsic advantages of this element, such as high intrinsic electron and hole mobility. In order to fabricate high performance devices, it is however essential to understand germanium surface chemistry and to find effective ways to clean and analyze its surface.

Surface treatment methods in particular have so far been developed for silicon surfaces, although approaches also have been made in order to treat germanium surfaces in order to characterize and visualize defects as contained.

One well known structural etching solution, already widely used for silicon substrates, is a dilute aqueous solution of an alkali dichromate, as for example described by F. Secco d'Aragona in *Journal of the Electrochemical Society* 119, No. 7, 948-951 (1972). This etch already has been used on germanium substrates with highly satisfactory results, such as good etch rate and reliable defect identification. However, the use of dichromate-containing solutions is considered as being unfavorable due to the toxic nature of the dichromate compounds, which are known to cause severe damages to human health. Accordingly, differing structural etching solutions have been developed for treating germanium surfaces, such as the etchant disclosed in *Applied Physics Letters*, Vol. 75, No. 19, pages 2909-2911, comprising acetic acid, nitric add, hydrofluoric acid, and iodine. A similar etchant is also disclosed in *Applied Physics Letters*, Vol. 85, No. 11, pages 1928-1930.

Other etchants employed for germanium surfaces are solutions comprising hydrofluoric acid, hydrogen peroxide, and acetic acid in a 1:1:1 ratio as well as the simple use of hydrochloric acid and hydrofluoric acid, respectively, for removing oxide coatings on germanium surfaces, as disclosed in *Applied Physics Letters*, Vol. 60, No. 7, pages 844-846, and *Applied Physics Letters* 88, the article extending from page 021903-1 to 021903-3.

Finally, a two-step treatment regiment has been disclosed in *ECS Transactions*, 6(4), 263-269 (2007), comprising a dip of a germanium surface in a mixture of hydrofluoric acid, nitric acid, and acetic acid, followed by a short dip into hydrogen peroxide.

While most of the etchant compositions disclosed above show a suitable ability for treating germanium surfaces, it is nevertheless still required to improve the quality of the surface treatment, in order to enable a high quality characterization of the treated surface and also enabling the treatment of rather thin germanium substrates, such as GeOI substrates, without suffering from the drawback of undesired film delamination due to undesired etching progress.

DISCLOSURE

Accordingly, the present invention aims at providing a method for treating germanium surfaces, enabling a highly reliable way of characterizing the surface, in particular characterizing defects on the surface, while, at the same time, also enabling the safe treatment of thin germanium substrates without the danger of film delamination.

The above object has been solved with the method for treating germanium surfaces as defined in claim 1. Preferred embodiments are given in sub-claims 2 to 9. The present invention furthermore provides a kit-of-parts comprising two solutions as defined in claim 10, which are to be used in the method in accordance with the present invention. Preferred embodiments, again, are defined in the respective sub-claims 11 to 15.

Further preferred embodiments are defined in the following specification.

DETAILED DESCRIPTION OF THE INVENTION

Figure 1:
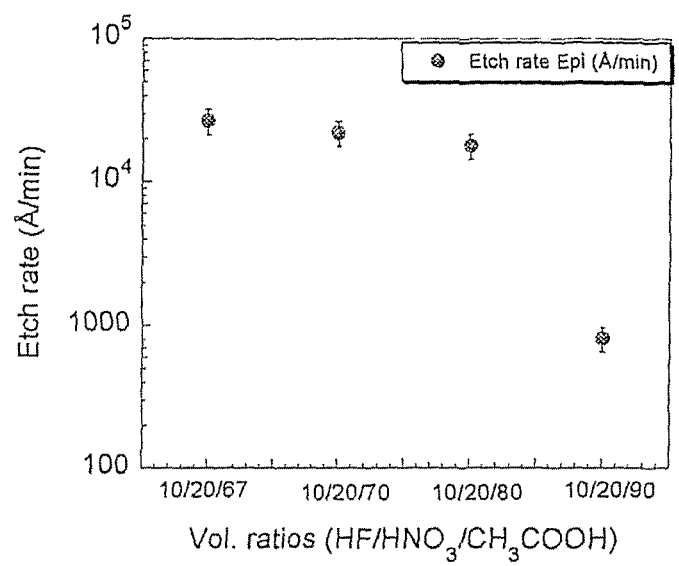
FIG. 1 shows the results of experiments displaying the dependency of the etch rate from the volume ratio of hydrofluoric acid/nitric acid/acetic acid. The volume ratios as referred to in FIG. 1 concern a mixture prepared by using hydrofluoric acid with a concentration of 49 vol %, nitric acid with a concentration of 70 vol %, and pure acetic acid.

The method in accordance with the present invention is characterized in that a germanium surface is treated in a method comprising the following steps:

(1) treating the germanium surface with an iodine- and bromine-free solution comprising hydrofluoric acid, nitric acid, and acetic acid, followed by
(2) treating the germanium surface with a solution comprising hydrofluoric acid, hydrogen peroxide, water, and a halogen compound.

It has been surprisingly found that with a method as defined above, a highly satisfactory surface treatment of germanium substrates can be obtained, without encountering the danger of film delamination with thin germanium substrates, wherein furthermore the characterization of defects is highly satisfactory and correlates, for example, to defect characterization obtainable with the disadvantageous chromate comprising prior art etchant compositions.

Between steps (1) and (2) of the method in accordance with the present invention, the germanium surface may be rinsed with water, preferably deionized water.

In the following, preferred embodiments for the solutions to be employed in the method in accordance with the present invention are described, together with preferred treatment conditions. These embodiments not only apply to the method in accordance with the present invention, but also to the kit-of-parts as claimed.

Solution Employed in Step (1)

The solution as applied in step (1) is an iodine-and bromine-free solution comprising hydrofluoric acid, nitric acid, and acetic acid. Preferably, the solution consists of hydrofluoric acid, nitric acid, acetic acid, and water (the water originates from the fact that, in particular, hydrofluoric acid and nitric acid are employed in the form of aqueous solutions, it is however preferred that no additional water is added). It is particularly preferred when the constituents for the solution to be employed in step (1) are selected among hydrofluoric acid solutions in water having a hydrofluoric acid concentration of from 40 to 49 vol %, preferably 49 vol %; a nitric acid solution in water having a concentration of nitric acid of from 50 to 70 vol %, preferably 70 vol %; and an aqueous acetic acid having an acetic acid concentration of from 70 to 99 vol %, preferably 99 vol %. If in the following volume ratios are described for the various constituents of the solutions, they preferably refer to volume ratios of a hydrofluoric acid with a concentration of 49 vol %, a nitric acid solution in water having a concentration of nitric acid of 70 vol %, and an aqueous acetic acid having an acetic acid concentration of 99 vol %.

The volume ratio of hydrofluoric acid to nitric acid typically is from 1:1 to 1:5, preferably 1:1.5 to 1:4, and in particular about 1:2. The volume ratio of hydrofluoric acid to acetic acid typically is from 1:4 to 1:10, preferably 1:5 to 1:8, more preferably 1:6 to 1:7.5, and in particular about 1:6.7.

Accordingly, a particularly preferred solution to be employed in step (1) is a solution consisting of hydrofluoric acid (49 vol % in water), nitric acid (70 vol % in water), and pure acetic acid (99 vol % or more) with a volume ratio of hydrofluoric acid/nitric acid/acetic acid being 1:2:6.7.

Typically the temperature for carrying out step (1) of the method in accordance with the present invention is lower than room temperature (20° C.) and, in particular it is preferred when the temperature is from 2° C. to 15° C., more preferably 5° C. to 13° C., and in particular about 8° C. This temperature refers to the temperature of the solution and it is preferred when also the atmosphere in contact with the solution and the germanium substrate to be treated has a temperature within the range as outlined above.

The treatment time is selected depending on the desired thickness of the germanium substrate to be etched away, and typically the treatment time of several minutes. As indicated above, after the treatment according to step (1) in accordance with the present invention the treated surface preferably is rinsed with water, typically deionized water for several minutes. The temperature of this rinsing is-not critical. Prior to the treatment with the solution as defined for step (1) of the present invention, the germanium substrate may be pre-treated, typically by rinsing with deionized water and/or immersing the surface for a few seconds in a bath comprising an aqueous solution of hydrofluoric acid, typically at a hydrofluoric acid concentration of 49 vol %.

The solution to be employed in step (2) of the method in accordance with the present invention is a solution comprising hydrofluoric acid, hydrogen peroxide, water, and a halogen compound. Preferably, the halogen compound is a chlorine-containing compound and even more preferably, this compound is an inorganic halogen-containing, preferably chlorine-containing, compound. A particular preferred example of such a compound is hydrochloric acid, which may preferably be employed in the form of a hydrochloric acid solution in water, having a hydrochloric acid concentration of above 20 vol %, more preferably above 30 vol %, and in particular 37 vol %.

The hydrofluoric acid to be employed in accordance with the present invention for the solution to be employed in step (2) is selected among the hydrofluoric acid embodiments as described above for the solution of step (1). Hydrogen peroxide to be employed in the solution for step (2) of the present invention preferably is an aqueous hydrogen peroxide solution, typically with a hydrogen peroxide concentration of above 20 vol %, more preferably 25 vol %, and in particular about 29 vol %.

Preferably the second solution to be applied in step (2) consists of hydrofluoric acid, hydrogen peroxide, water, and hydrochloric acid, and with respect to the ratios of the four components the following applies. As far as volume ratios are referred to in the following they preferably refer to volume ratios where the respective components are aqueous hydrofluoric acid with a concentration of 49 vol %, aqueous hydrogen peroxide with a concentration of 29 vol %, and aqueous hydrochloric acid with a concentration of 37 vol %.

Typically the volume ratio of hydrofluoric acid to hydrogen peroxide is from 1:1 to 1:5, preferably 1:2 to 1:4, and in particular 1:2. The volume ratio of hydrofluoric acid to water is typically in the range of from 1:5 to 1:25, preferably 1:8 to 1:20, more preferably 1:9 to 1:18, and in particular 1:10 to 1:12. The final concentration of the halogen compound, calculated as Cl content, is typically below 15 vol %, such as below 10 vol %, i.e., in embodiments from 3 to 7 vol %, and in particular about 5 vol %.

The temperature at which step (2) of the method in accordance with the present invention is carried out typically, again, is below room temperature, preferably from 2° C. to 20° C., more preferably from 5° C. to 15° C., and in particular about 8° C. The definition as provided above for step (1) with respect to the temperature of the solution employed and the atmosphere also applies with respect to step (2) described here.

The treatment time in step (2) is considerably shorter, compared with step (1), and typically only a few seconds are required in order to obtain germanium substrate surfaces ready for visual inspection. Accordingly, treatment times from 1 to 60 seconds are contemplated, such as from 1 to 30 seconds, and in embodiments even only 1 to 10 seconds.

After step (2) the germanium substrate surface may be rinsed with water and may be dried in accordance with conventional processes.

Steps (1) and (2) as described above preferably are carried out in a manner in that the germanium substrate is dipped with the surface into the respective solution employed during the step (1) and/or (2).

Surprisingly it has been found that the two-step procedure in accordance with the present invention enables a good surface treatment of germanium substrates, even thin germanium substrates, without giving rise to film delamination, while enabling with a high reliability the identification of defects on the treated surfaces.

As defined in the claims, the present invention also provides a kit-of-parts comprising two solutions (1') and (2'), wherein these two solutions correspond to the solutions as described above for steps (1) and (2), respectively, for the method in accordance with the present invention. This kit-of-parts provides the required solutions for the novel and inventive method for treating germianium surfaces in accordance with the present invention. The preferred embodiments as outlined above in connection with the method also apply with respect to the kit-of-parts as claimed here.

Figure 2:
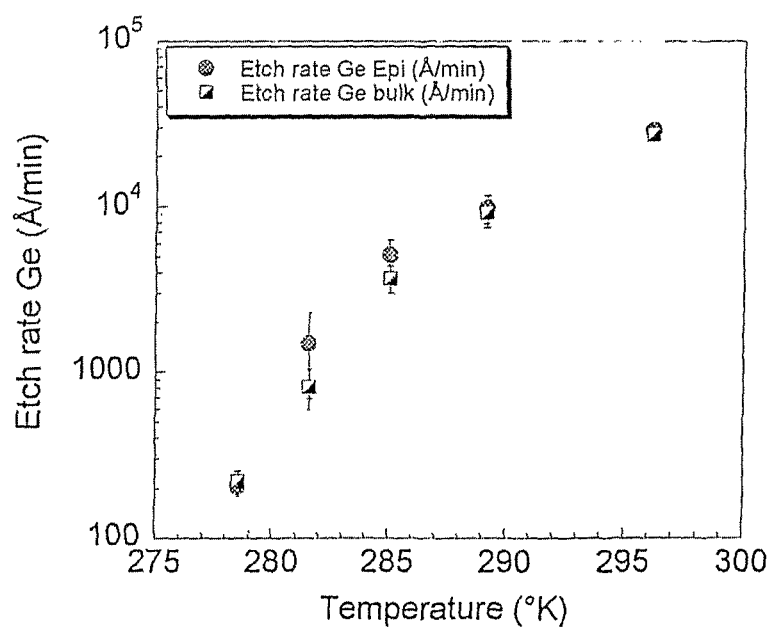
FIG. 2 displays the dependency of the etch rate from the temperature of the solution employed in step (1) of the method in accordance with the present invention.
Figure 3:
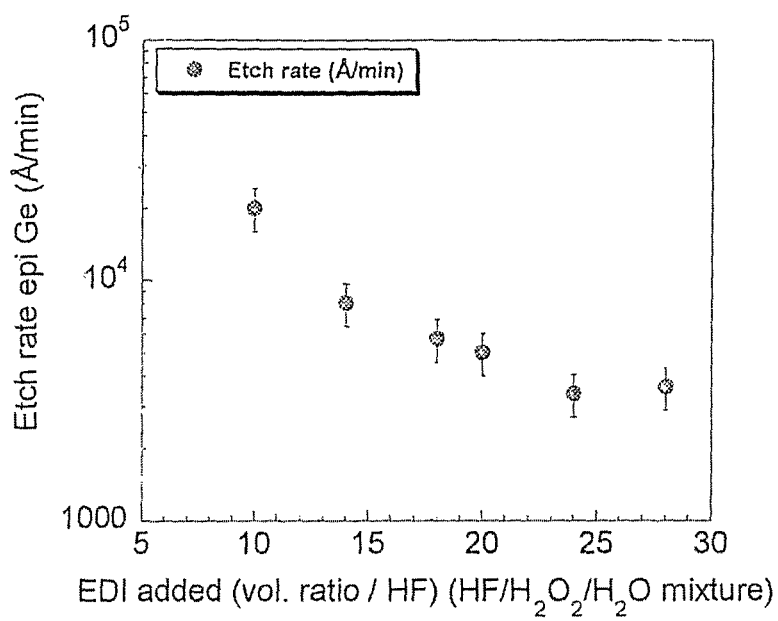
FIG. 3 shows the dependency of the etch rate from the volume of water added to the second solution employed in accordance with the present invention.
Figure 4:
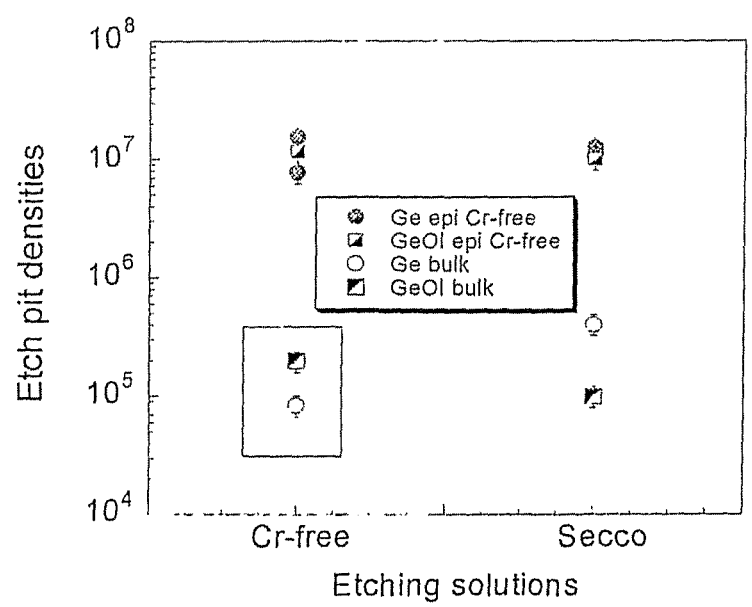
FIG. 4, finally, displays results concerning etch pit densities as obtained with chromium-free solutions in accordance with the present invention, compared with prior art chromium-containing solutions.

The present invention, as indicated above, enables an improved treatment of germanium surfaces, enabling the visual observation of the treated surface in order to reveal defects. The reliability of the method in accordance with the present invention is similar to the reliability of the prior art chromium-containing etchant, i.e., highly satisfactory. FIG. 4, as contained herein, in this respect clearly shows that with the method in accordance with the present invention etch pit densities can be obtained on germanium surfaces corresponding to the etch pit densities as obtained with the prior art solution, revealing that the method in accordance with the present invention enables the same degree of accuracy with respect to the revealing of etch pits, i.e., defects on the surface. FIGS. 1 to 3, as contained herein, furthermore clearly show that within the preferred compositional ratios and within the preferred temperature ranges, highly suitable etch rates can be obtained, securing that the desired effect is obtained without endangering the integrity of GeOI substrate, for example, by delamination.

In the following, a preferred method for treating germanium surfaces is disclosed:
(1) The wafer is immersed for a few seconds into a hydrofluoric acid bath (49 vol %) to remove the native oxide layer and to start revelation.
(2) The wafer is immersed into the first etch solution (step (1)) in accordance with the present invention, wherein the etch solution is adjusted to provide an etch rate of from 3,000 to 6000 A/min, in order to etch the desired amount of germanium.
(3) The wafer is rinsed with deionized water for several minutes.

The wafer is immersed into the second etch solution (step (2)) for a few seconds in order to delineate the defects. Immersing time is adjusted, but in any case, it is ensured that no film delamination occurs.

As outlined above, the present invention provides a method for treating germanium surfaces, enabling a good control of the etch rates while providing highly satisfactory etch results. Compared with prior art etchants, the present invention enables typically a better control of the etching with results being similar or better, in comparison with the chromium-containing etchant disclosed in the prior art. With thin germanium layers the etch results, such as etch pit densities, are similar to densities found with chromium-containing solutions. With thicker germanium layers, such as bulk germanium substrates, the defects are even better delineated, compared with the chromium-containing prior art etchant, so that even, in addition to the replacement of the undesired chromium-containing etchant, a further advantage is associated with the present invention.

The invention claimed is:

1. A method for treating a germanium substrate, comprising the following steps:
   (1) treating a germanium surface of the germanium substrate with an iodine- and bromine-free solution comprising hydrofluoric acid, nitric acid, and acetic acid, followed by
   (2) treating the germanium surface with a solution comprising hydrofluoric acid, hydrogen peroxide, water, and a halogen compound.

2. The method of claim 1, wherein the solution employed in step (1) consists of hydrofluoric acid, nitric acid, and acetic acid.

3. The method of claim 1, wherein the solution used in step (2) consists of hydrofluoric acid, hydrogen peroxide, water, and a halogen compound.

4. The method of claim 1, wherein the halogen compound comprises hydrochloric acid.

5. The method of claim 1, wherein step (1) is carried out at a temperature in a range extending from 5° C. to 13° C.

6. The method of claim 1, wherein step (2) is carried out at a temperature in a range extending from 5° C. to 15° C.

7. The method of claim 1, wherein a rinsing step with deionized water is provided between steps (1) and (2).

8. The method of claim 1, wherein a volume ratio of hydrofluoric acid to nitric acid in the solution employed in step (1) is from 1:1 to 1:5.

9. The method of claim 1, wherein a volume ratio of hydrofluoric acid to hydrogen peroxide in the solution employed in step (2) is from 1:1 to 1:5.

* * * * *